United States Patent
Maruo et al.

(10) Patent No.: US 7,074,421 B2
(45) Date of Patent: Jul. 11, 2006

(54) MEMBER FOR APPLICATION OF OINTMENT AND OINTMENT PATCH EMPLOYING THE SAME

(75) Inventors: Susumu Maruo, Tokyo (JP); Osafumi Hidaka, Tokyo (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/031,409

(22) PCT Filed: Jun. 5, 2001

(86) PCT No.: PCT/JP01/04735

§ 371 (c)(1),
(2), (4) Date: Jan. 18, 2002

(87) PCT Pub. No.: WO01/93839

PCT Pub. Date: Dec. 13, 2001

(65) Prior Publication Data

US 2003/0012808 A1    Jan. 16, 2003

(30) Foreign Application Priority Data

Jun. 6, 2000    (JP)    ............................. 2000-168811

(51) Int. Cl.
*A01N 25/34* (2006.01)
*A61K 9/00* (2006.01)
*A61K 9/70* (2006.01)
*A61L 15/16* (2006.01)

(52) U.S. Cl. ...................... 424/402; 424/400; 424/443; 424/447; 424/449

(58) Field of Classification Search ................ 424/402, 424/443, 447, 400, 449
See application file for complete search history.

(56) References Cited

U.S. PATENT DOCUMENTS

| 5,045,553 A | * | 9/1991 | Ueda et al. |
| 6,455,067 B1 | * | 9/2002 | Woo et al. |

FOREIGN PATENT DOCUMENTS

| EP | 1177786 A | 2/2002 |
| JP | 61-210027 | 9/1986 |
| JP | 3-161431 | 7/1991 |
| JP | 4-257516 | 9/1992 |
| JP | 5-238931 | 9/1993 |
| JP | 7-48249 | 2/1995 |
| JP | 7-048249 | 2/1995 |
| JP | 7-97315 | 4/1995 |
| JP | 7-097315 | 4/1995 |
| JP | 8-291054 | 11/1996 |

OTHER PUBLICATIONS

Database WPI Section Ch, Week 198307 Derwent Publications Ltd., London, GB; Class A96, AN 1983-15774K XP002280271 & JP 58 000913 A (Nitto Electric Ind Co) Jan. 6, 1983.

(Continued)

*Primary Examiner*—Humera N. Sheikh
(74) *Attorney, Agent, or Firm*—Sughrue Mion, PLLC

(57) ABSTRACT

An ointment patch includes a support, an ointment, and optionally, a separator. In this ointment patch, the ointment is coated on one surface of the support in an amount of 0.1 mg to 200 mg per 1 cm² of the support, and the support has a thickness of 1 μm to 2000 μm and 50% modulus of 5 g/cm to 600 g/cm.

8 Claims, 1 Drawing Sheet

OTHER PUBLICATIONS

Database WPI Section Ch, Week 199134 Derwent Publications Ltd., London, GB; Class A96, AN 1991-248685 XP002280272 & JP 03 161432 A (Lion Corp) Jul. 11, 1991.
Database WPI Section Ch, Week 199134 Derwent Publications Ltd., London, GB; Class A96, AN 1991-248686 XP002280273 & JP 03 161433 A (Lion Corp) Jul. 11, 1991.
Database WPI Section Ch, Week 198938 Derwent Publications Ltd., London, GB; Class A11, AN 1989-273363 XP002280274 & JP 01 197434 A (SS Pharmaceutical KK) Aug. 9, 1989.
Copy of European Search Report dated Jun. 2, 2004.

* cited by examiner

MEMBER FOR APPLICATION OF OINTMENT AND OINTMENT PATCH EMPLOYING THE SAME

This application is a 371 of PCT/JP01/04735 filed Jun. 05, 2001. This application claims priority to foreign Japanese Application No. JP 2000-168811 filed Jun. 06, 2000.

1. Technical Field

The present invention relates to an ointment applicator for effectively administering ointments and an ointment patch using such an ointment applicator.

2. Background Art

Ointments allow us to apply drugs in a desired manner depending on skin morphology and degree of skin damage. For this reason, ointments are widely used as a way of percutaneously administering drugs. One drawback of ointments is that, because of their spreadablity, ointments may inadvertently be transferred elsewhere through contact with, for example, clothes. This may result in a reduced efficacy of the drug and secondary side effects. To alleviate this problem, ointment patches have been proposed in which ointment is coated onto a support (Japanese Patent Laid-Open Publication No. Hei 4-257516, Japanese Patent Laid-Open Publication No. Hei 7-97315, Japanese Patent Laid-Open Publication No. Hei 8-291054, Japanese Utility Model Registration No. 3066506). The approaches disclosed in these publications are each effective in preventing the ointment from being transferred elsewhere. However, these ointment patches are accompanied by problems such as uncomfortableness upon application to skin, reduced mechanical strength or reduced drug-releasing ability of the ointment patch due to migration of the ointment component to the support. Therefore, the ointment patches without these problems have yet to be developed.

Accordingly, it is an objective of the present invention to provide an ointment applicator for administering ointments to skin that can prevent transfer of ointment elsewhere as well as reduction in its drug releasing ability, without causing uncomfortableness when applied to skin. It is also an objective of the present invention to provide an ointment patch that makes use of the ointment applicator.

The present inventors have conducted extensive studies in an effort to achieve such an objective and completed the present invention.

DISCLOSURE OF THE INVENTION

In a first aspect of the present invention, there is provided an ointment patch including a support, an ointment, and optionally, a separator, wherein the ointment is coated on one surface of the support in an amount of 0.1 mg to 200 mg per 1 cm$^2$ of the support and the support has a thickness of 1 μm to 2000 μm and a 50% modulus of 5 g/cm to 600 g/cm.

In a second aspect of the present invention, there is provided an ointment applicator including a support, and an adhesive layer disposed on one surface of the support to allow the ointment applicator to adhere to skin with a part of the applicator, wherein the support has a thickness of 1 μm to 2000 μm and a 50% modulus of 5 g/cm to 600 g/cm

BEST MODE FOR CARRYING OUT THE INVENTION

Figure 1:
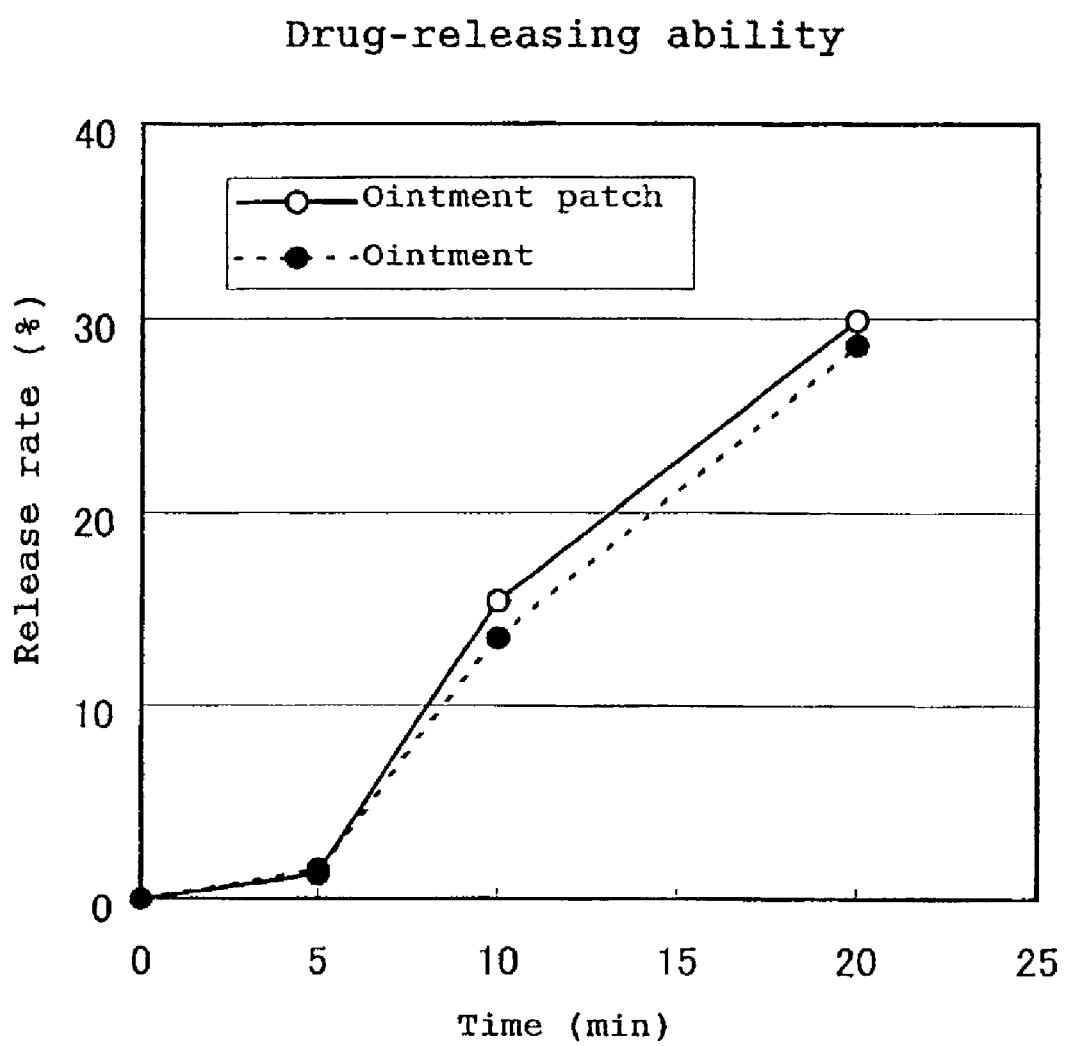
FIG. 1 shows the comparison of drug-releasing ability between an ointment (ointment only) and an ointment patch of the present invention measured in a reference example 1. As can be seen from FIG. 1, they have comparable drug releasing abilities.

In a first embodiment of the present invention, an ointment may be applied in an amount of 0.1 mg to 200 mg per 1 cm$^2$ of a support (0.1 mg/cm$^2$ to 200 mg/cm$^2$) Preferably, the ointment is applied in an amount of 0.5 mg to 100 mg per 1 cm$^2$ of the support (0.5 mg/cm$^2$ to 100 mg/cm$^2$)

If the amount of the ointment is less than 0.1 mg/cm$^2$, it is difficult to uniformly coat the ointment throughout the surface of the support and it is no longer possible for ointment patches to administer a drug in uniform dosages. Conversely, if the amount of the ointment exceeds 100 mg/cm$^2$, the ointment may be pushed out from the support when external forces, such as pressure, are exerted on the ointment patch. This increases the likelihood that the ointment is transferred elsewhere and, therefore, is unfavorable.

It is important that the support has a thickness of 1 μm to 2000 μm and a 50% modulus of 5 g/cm to 600 g/cm in the present invention. Preferably, the support has a thickness of 5 μm to 1000 μm and a 50% modulus of 10 g/cm to 500 g/cm.

If the support has a thickness less than 1 μm, the support may be damaged while being rubbed against other objects especially when the ointment patch is applied to joint areas such as elbows or knees, and, as a result, the ointment is more likely to be transferred elsewhere. In contrast, the support with the thickness greater than 2000 μm tends to cause uncomfortableness when the ointment patch is applied to skin. Also, the ointment patch tends to come off due to rubbing when applied to joint areas.

The 50% modulus of the support that is less than 5 g/cm is unfavorable since it increases the tendency that the support tears or ruptures, especially when the ointment patch is applied to body areas, such as joint areas, that go through rigorous movements. In contrast, the 50% modulus of the support that is greater than 600 g/cm can cause twitching feeling and uncomfortableness.

In addition, it is important that the ointment is applied to the support in an amount of 0.1 mg/cm$^2$ to 200 mg/cm$^2$ and the support has a thickness of 1 μm to 2000 μm and a 50% modulus of 5 g/cm to 600 g/cm in the present invention. When these conditions are met, the ointment patch of the present invention, which includes the support, the ointment, and optionally, a separator, and can prevent transfer of the ointment elsewhere without causing uncomfortableness when applied to skin, is achieved.

The ointment patch of the present invention, which does not include any layer structure, generally referred to as an intermediate layer (which may be referred to as an intermediate layer, hereinafter), between an ointment-coated surface and skin, is capable of applying the ointment directly to skin, thereby preventing reduction in its drug releasing ability. In addition, unlike the ointment patches with an intermediate layer, the ointment patch of the present invention can prevent loss of the ointment or loss of drugs present in the ointment, caused by the ointment being absorbed by, or sticking to, the intermediate layer. Having dispensed with the intermediate layer, the ointment patch of the present invention further achieves improved adhesion to skin.

Preferably, the supports of the present invention are attached to one another via an self-adhesion force of 150 g/12 mm or less, particularly 100 g/12 mm or less, in order to prevent the supports from closely adhering to one another when the ointment patch is applied to joint areas such as elbows and knees.

Further, the support of the present invention preferably has a stretch recovery of 50% or higher when stretched by as much as 10% of its length, which is equivalent to the stretch of skin experienced in daily life. Preferably, the support of the present invention has a stretch recovery of 70% or higher since a low stretch recovery can result in unfavorable appearances of the ointment patch after the patch has been applied to skin.

Preferably, the support of the present invention has a water vapor permeability of 100 $g/m^2/24$ hr or higher, particularly 600 $g/m^2/24$ hr or higher. The water vapor permeability less than 100 $g/m^2/24$ hr may cause itchy skin, eczema, and dermatitis as it becomes stuffy inside the ointment patch.

The support of the present invention may be of any material and shape, provided that the support has the aforementioned characteristics and the ointment does not penetrate through to the opposite side of the ointment-coated surface. Examples of the support include film, fabric, knit, non-woven fabric and paper, each of which is made from, for example, polyester, polyolefin, polyurethane, cellulose, and cross-linked copolymers of vinyl acetate and acrylic acid. Of these, film is particularly preferred for easily preventing the ointment from penetrating the ointment patch. The film may be provided in any form of a non-porous membrane, a microporous membrane and a porous membrane utilizing independent foam.

The support of the present invention may be those obtained by overlaying the film with cloth such as fabric, knit, non-woven fabric and paper. The cloth may be of any cloth material that has 50% modulus (i.e., stretchability) of 5 g/cm to 600 g/cm. Examples of such cloth include those made of-fabric, knit, non-woven fabric and paper with a basis weight (METSUKE) of 5 to 300 $g/m^2$ and having a fiber diameter of 0.5 to 1 μm.

It is preferred that the ointment, the film and the cloth be overlaid on top of one another in this order when the cloth is used for the purposes of firming the ointment patch and improving the texture of the ointment patch. Also, it is preferred that the same components be overlaid on top of one another in the order of the ointment, the cloth, and the film when the cloth is used for the purpose of improving uniformity of the applied ointment.

The film and the cloth are overlaid on top of one another either by interposing a layer of a sticky agent between the film and the cloth, by heat-pressing the two components against each other, or by coating the film on top of the cloth.

Preferably, the support of the present invention includes a copolymer of a vinyl acetate and an acrylic acid which is obtained by copolymerizing a vinyl acetate, an alkyl ester of a (meth)acrylic acid with an alkyl group having 4 to 14 carbon atoms on average, and a (meth)acrylic acid in amounts of 0 to 90 wt %, 10 to 97 wt %, and 0 to 15 wt %, respectively, and it is preferred that the copolymer be formed by cross-linking the copolymer.

The processes for forming cross-linkages in the copolymer include one which applies UV or gamma-ray to form cross-linkages or one in which a cross-linking agent, such as anhydrous silicic acid, a multi-functional vinyl monomer, diglycidylether, a polyisocyanate compound, an organometallic salt, or a metal chelate compound, is added to form cross-linkages.

In order to prevent the ointment patch of the present invention from being wrinkled upon application to skin, a peelable liner may be disposed on a surface of the support that is opposite to the ointment-coated surface. Preferably, the liner can be peeled off the support with a peeling force of 50 g/cm or less. The liner may be of any material and shape, provided that the requirement for the peeling force (50 g or less) is met. Examples of the preferred liner include a separating film or separating paper having a thickness of 10 to 100 μm and made from materials such as polyester, polyethylene, polyvinyl chloride, cellulose, or polyethylene vinyl acetate. Also included are cloth, fabric, knit, and non-woven fabric having a basis weight (METSUKE) of 5 to 300 $g/m^2$ and made from materials such as polyester, nylon, urethane, or cellulose.

While the liner, which is integrally overlaid on top of the support, may be cut to the same size as the support, it may be sized larger than the support or it may be disposed to cover only a part of the support.

It is important that the support is sufficiently flexible and is non-ointment-migration-permissive. This is because, if the ointment component migrates to the support and acts on the support as a plasticizer, mechanical properties of the support may deteriorate and the efficacy of the drug may be reduced due to the reduced drug-releasing ability.

By "the support is non-ointment-migration-permissive," it is meant that the ointment has a low affinity for the support. It is difficult to express this affinity using a single parameter since the affinity is determined by various factors including chemical structure, functional groups, tendency to form hydrogen bonds, and glass transition temperature. When the solubility parameters are used as indices of the affinity, the non-ointment-migration-permissiveness of the support is achieved by employing combinations of a particular ointment and a particular support so that the difference between the solubility parameter of the ointment and that of the support is preferably 1.0 or larger, and particularly 2.0 or larger.

In order to ensure that the ointment patch stays at the position where it is initially applied and does not move out of the position when it is applied to joint areas such as elbows and knees, an adhesive layer is preferably disposed on the support on the same side as the ointment-coated surface to allow the ointment patch to adhere to skin with a part of the patch. The adhesive layer may be either arranged throughout the circumference of the ointment patch, intermittently arranged along the circumference of the ointment patch, or arranged on the opposing two sides or arranged in stripes or lattice when the ointment patch is rectangular.

The adhesive layer is properly sized depending on the shape and the size of the ointment patch. In order to enable the effective administration of the ointment while maintaining the ointment patch's adhesiveness to skin, the size of the adhesive layer is preferably from 3% to 70%, particularly from 5% to 60%, relative to the total area of the support.

The adhesive layer may be arranged adjacent to the ointment, or a buffer area may be arranged between the two to prevent the adhesive layer and the ointment from abutting one another.

The ointment patch of the present invention may be designed such that it can be folded onto itself to bring the ointment-coated surface into contact with itself. In this manner, a separator for protecting the ointment surface during storage can be dispensed with. In particular, when the ointment patch is designed in such a manner that the ointment patch, which includes the adhesive layer for allowing the ointment patch to adhere to skin with an entire surface of the patch or a part of the patch at the ointment coating surface, can be folded onto itself along its center line to bring the ointment-coated surface into contact with itself to eliminate the need for the separator, a different separator to protect the surface of the adhesive layer may be provided.

This separator may have one surface treated with a parting treatment such as silicone resin or fluoride resin. The separator may be disposed on each surface of the adhesive layer, or it may have both of its surfaces treated with the parting treatment to provide protection for a plurality of surfaces of the adhesive layer.

In the ointment patches that have eliminated the need for the above-described separator, the adhesive layer may be folded in a direction opposite to the folding direction that brings the adhesive layer into contact with itself. In other words, the adhesive layer is folded so that the ointment-coated surface faces outward. Also, the ointment patch can be made more handleable by disposing adhesive layers with different areas.

In the present invention, the ointment may first be applied to the application site such as skin, and the ointment applicator, which includes the flexible support having the adhesive layer for allowing the ointment applicator to adhere to skin with a part of the applicator, may subsequently be applied. This pre-application of the ointment to the application site, such as skin, makes it possible to adjust the amount of the applied ointment depending on symptoms.

The same effects as with the above-described ointment patch of the present invention, which includes the support that is pre-coated with the ointment, can be obtained with the ointment applicator, which includes the support that is not pre-coated with the ointment, by first applying the ointment to the application site and subsequently covering the application site with the flexible ointment applicator.

The sticky agent that constitutes the adhesive layer of the present invention is not limited to particular types of adhesive and may be any conventional adhesive that shows certain adhesiveness to skin. Examples include rubber-based sticky agents containing as a major component a material such as silicone rubber, polyisoprene rubber, styrene-butadiene copolymer rubber, acrylic rubber, and natural rubber; vinyl-based sticky agents such as polyvinylalcohol, polyacrylic acid, and polyvinyl acetate; and sticky agents based on esters of acrylic acids that contain an alkyl ester of acrylic acid as a major component. Of these, the sticky agents based on esters of acrylic acids are preferred because of their adhesion characteristics, economical efficiency and stability. In particular, copolymers based on alkyl esters of (meth)acrylic acids obtained by copolymerizing an alkyl ester of (meth)acrylic acid having 4 to 20 carbon atoms and (meth)acrylic acid in amounts of at least 80 to 98 mol % and 2 to 20 mol %, respectively, are preferred because of their low irritancy to skin, appropriate stickiness, adhesiveness, internal cohesion, and excellent solvent resistance.

Examples of the alkyl ester of (meth)acrylic acid include butyl(meth)acrylate, amyl(meth)acrylate, hexyl(meth)acrylate, heptyl(meth)acrylate, octyl(meth)acrylate, nonyl(meth)acrylate, decyl(meth)acrylate, and 2-ethylhexylacrylate.

The stickiness of the sticky agents that constitute the adhesive layer of the present invention is not limited to a particular range, provided that it ensures the sufficient stickiness to skin and does not cause pain when the ointment patch/applicator is removed after use. The stickiness is preferably in the range of 40 g to 400 g as measured by the stickiness tests for Japanese Pharmacopeia adhesive tapes.

The ointment for use in the present invention may be any ointment that can be provided in a semi-solid form and shows spreadablility at room temperature. Examples of the ointment include oil ointments, emulsion ointments, and water-soluble ointments. Each of these ointments may further contain various known additives including stabilizers, surfactants, plasticizers, antioxidants, algefacients, antiseptics, pH conditioners, fragrances, or dissolving agents.

Examples of the drug for use as a pharmacologically active ingredient in the ointment of the present invention include, but are not limited to, antiphlogistics and analgesics such as esters of salicylic acid, indomethacin, ketoprofen, and Felbinac; sex hormones such as estradiol, progesterone, and testosterone; anti-viral agents such as aciclovir, and vidarabine; hormone-based anti-dermatosis agents such as betamethasone valerate, and dexamethasone; vitamins such as vitamin A, vitamin C, and vitamin E; antibiotics such as pimaricin, and tetracycline; local anesthetics such as lidocaine; anti-psoriatic agents such as tacalcitol; anti-atopic dermatitis agents such as tacrolimus hydrate; and disinfectants such as povidone-iodine.

When necessary, a separator may be used in the present invention to protect the ointment surfaces while the ointment patches are stored. The separator may be of any material and shape, provided that it can readily be peeled off the ointment patch upon use and prevent migration of the ointment to the separator. Preferred examples of the separator include film, fabric, knit, non-woven fabric, and paper which are made of polyester, polyolefin, polyurethane, or cellulose and whose surfaces are treated with a parting treatment such as fluoride resin or silicone resin.

It is preferred that the separator be readily peeled off the ointment patch upon use.

Preferably, the separator can be peeled off the ointment patch with a peeling force of 50 g/cm or less, more preferably 30 g/cm or less, in a 180-degree peeling test.

The separator may be of any thickness unless it hinders handling of the ointment patch. The separator has a preferred thickness of 10 µm to 2000 µm.

EXAMPLES

The present invention will now be described in further detail with reference to Examples, which are provided by way of example only and are not intended to limit the scope of the invention in any way.

Throughout Examples, the term "parts" and % represent parts by weight and by weight, respectively. The 50% modulus was determined by measuring load per unit width of a sample when the sample was stretched by 50% of its length at a rate of 100%/min on a tensile tester. The water vapor permeability was determined by placing calcium chloride in a weighing bottle, covering the top of the bottle with the sample, leaving the covered bottle at 40° C. under 90% RH, and measuring increases in weight per unit time and per unit area of the sample.

EXAMPLE 1

15 g of 5 wt % acetylacetone solution of tris (2,4-pentanedionato)aluminum was added to 200 g of 20 wt % ethylacetate solution of a vinyl acetate copolymer composed of 70 wt % vinyl acetate, 27.5 wt % 2-ethylhexylacrylate, and 2.5 wt % acrylic acid. The resulting solution was coated to give a film thickness of 10 µm to obtain cross-linked vinyl acetate copolymer film. The film has the 50% modulus of 112 g/cm and the water vapor permeability of 2510 g/m²/day. This film was used as a support, and one surface of the film was then coated with an ointment composed of 95 wt % white Vaseline and 5 wt % liquid paraffin with the coating amount of 1.5 mg/cm². This completed an ointment patch. When the ointment patches were applied to forearms of subjects (n=3), no transfer of the ointment elsewhere was observed and no significant uncomfortableness experienced. Also, no migration of the ointment component to the support was observed and no change observed in the 50% modulus of the support.

EXAMPLE 2

An ointment patch was obtained in the same manner as in Example 1, except that polyester elastomer film, which had a film thickness of 14 μm, 50% modulus of 74 g/cm, and water vapor permeability of 1260 g/m²/day and included hard segments formed from polybutylene phthalate and soft segments formed from triethylene glycol, was used as the support. When the ointment patches were applied to forearms of subjects (n=3), no transfer of the ointment elsewhere was observed and no significant uncomfortableness experienced. Also, no migration of the ointment component to the support was observed and no change observed in the 50% modulus of the support.

EXAMPLE 3

Using an acrylic sticky agent, a piece of non-woven fabric, formed from a polyester elastomer having a basis weight (METSUKE) of 35 g, was overlaid on one surface of the cross-linked vinyl acetate copolymer film of Example 1 to obtain a support. The film has 50% modulus of 130 g/cm and water vapor permeability of 2370 g m²/day. The support was then coated with the ointment on its non-woven fabric surface with the coating amount of 2 mg/cm² and was cut to the size of 50 cm² to obtain an ointment patch. When the ointment patches were applied to forearms of subjects (n=3), no transfer of the ointment elsewhere was observed and no significant uncomfortableness experienced. Also, no migration of the ointment component to the support was observed and no change observed in the 50% modulus of the support.

EXAMPLE 4

The cross-linked vinyl acetate film of Example 1 was cut to the size of 70 cm² and an acrylic sticky agent, containing 2-ethylhexylacrylate as a major component, was applied to the periphery of the film to cover 40% of the area of the support. The ointment was then applied to the support portion with the amount of 1.5 mg/cm² to obtain an ointment patch. When the ointment patches were applied to forearms of subjects (n=3), no transfer of the ointment elsewhere was observed and no significant uncomfortableness experienced. Also, no migration of the ointment component to the support was observed and no change observed in the 50% modulus of the support.

EXAMPLE 5

The support of Example 4 with the sticky agent layer was used as the ointment applicator. When the ointment applicators were applied to elbows of subjects (n=3) applied with an appropriate amount of an ointment, no transfer of the ointment elsewhere was observed and no significant uncomfortableness experienced. Furthermore, no migration of the ointment component to the support was observed and no change observed in the 50% modulus of the support.

Reference Example 1

As a therapeutic agent, an ointment containing 5% aciclovir (product name zovirax ointment) was coated onto the support of Example 1 with a coating amount of 11 mg/cm² to obtain an ointment patch. The ointment patch was cut to the size of 15 mmF to serve as a sample for the drug-releasing ability test. A piece of pig skin (product name ALLOASK (wound covering material)) was placed on a vertical diffusion cell and the sample was applied to a donor side of the vertical diffusion cell. An acceptor side was filled with 20 ml of water. The diffusion cell was then placed in a thermostatic chamber kept at 37° C. and samples were collected after 5, 10 and 20 minutes while the acceptor solution was stirred using a magnetic stirrer. The concentration of the therapeutic agent was measured for each sample in liquid chromatography to determine the drug-releasing ability. As a control, the same amount of the ointment as that used in the ointment patch was directly applied to another piece of pig skin, placed on the diffusion cell, over the same area as that covered by the ointment patch. As shown in FIG. 1, no significant decrease was observed in the ability of the ointment patch to release the drug and the ointment patch exhibited the drug-releasing ability comparable to the ointment.

INDUSTRIAL APPLICABILITY

As described thus far, through the use of the ointment patch, which includes the support, the ointment, and optionally the separator and in which the ointment is coated on one surface of the support in an amount of 0.1 mg to 200 mg per 1 cm² of the support and the support has a thickness of 1 μm to 2000 μm and 50% modulus of 5 g/cm to 600 g/cm, or through the use of the ointment applicator, which includes the support and the adhesive layer, disposed on one surface of the support to allow the ointment applicator to adhere to skin with a part of the applicator and in which the support has a thickness of 1 μm to 2000 μm and 50% modulus of 5 g/cm to 600 g/cm, transfer of the ointment elsewhere was prevented, as were the reduction in the drug-releasing ability and uncomfortableness experienced by users upon application of the ointment patch/ointment applicator to skin.

The invention claimed is:

1. An ointment patch consisting essentially of a support, an ointment, and optionally, a separator,
    wherein the ointment is coated on one surface of the support in an amount of 0.1 mg to 200 mg per 1 cm² of the support, and
    the support has a thickness of 1 μm to 2000 μm and 50% modulus of 5 g/cm to 600 g/cm, a water vapor permeability of 100 g/m²/24 hrs or higher, and is composed of a copolymer of vinyl acetate and acrylic acid, wherein the copolymer is obtained by copolymerizing a vinyl acetate, an alkyl ester of a (meth)acrylic acid with the alkyl having 4 to 14 carbon atoms on average, and a (meth)acrylic acid in amounts of 0 to 90 wt %, 10 to 97 wt %, and 0 to 15 wt %, respectively, and the copolymer is cross-linked.

2. The ointment patch according to claim 1, wherein the support is overlaid with cloth.

3. The ointment patch according to claim 1, wherein the support is non-ointment-migration-permissive.

4. The ointment patch according to claim 1, wherein the support includes an adhesive layer disposed on the ointment-coated surface of the support in order to allow the ointment patch to adhere to skin.

5. The ointment patch according to claim 1, wherein the ointment patch is folded onto itself to bring the ointment-coated surface into contact with itself.

6. An applicator consisting essentially of a support, and an adhesive layer disposed on one surface of the support to allow the applicator to adhere to skin, wherein the support has a thickness of 1 μm to 2000 μm, 50% modulus of 5 g/cm to 600 g/cm, a water vapor permeability of 100 g/m$^2$/24 hrs or higher, and is composed of a copolymer of vinyl acetate and acrylic acid, wherein the copolymer is obtained by copolymerizing a vinyl acetate, an alkyl ester of a (meth) acrylic acid with the alkyl having 4 to 14 carbon atoms on average, and a (meth)acrylic acid in amounts of 0 to 90 wt %, 10 to 97 wt %, and 0 to 15 wt %, respectively, and the copolymer is cross-linked.

7. The applicator according to claim 6, wherein the support is overlaid with cloth.

8. The applicator according to claim 6, wherein the support is non-ointment-migration-permissive.

* * * * *